US012774442B2

(12) United States Patent
Petrini et al.

(10) Patent No.: US 12,774,442 B2
(45) Date of Patent: Oct. 27, 2026

(54) THREE-DIMENSIONAL SUBSTRATE FOR MICROBIAL CULTURES

(71) Applicants: POLITECNICO DI MILANO, Milan (IT); UNIVERSITA' DEGLI STUDI DI PAVIA, Pavia (IT); UNIVERSITA' DEGLI STUDI DI TORINO, Turin (IT)

(72) Inventors: Paola Petrini, Milan (IT); Daniela Patricia Peneda Pacheco, Milan (IT); Natalia Andrea Suarez Vargas, Milan (IT); Federico Bertoglio, Pavia (IT); Sonja Visentin, Turin (IT); Livia Visai, Pavia (IT)

(73) Assignees: POLITECNICO DI MILANO, Milan (IT); UNIVERSITA' DEGLI STUDI DI PAVIA, Pavia (IT); UNIVERSITA' DEGLI STUDI DI TORINO, Turin (IT)

( * ) Notice: Subject to any disclaimer, the term of this patent is extended or adjusted under 35 U.S.C. 154(b) by 1125 days.

(21) Appl. No.: 17/416,161

(22) PCT Filed: Dec. 19, 2019

(86) PCT No.: PCT/IB2019/061120
§ 371 (c)(1),
(2) Date: Jun. 18, 2021

(87) PCT Pub. No.: WO2020/128965
PCT Pub. Date: Jun. 25, 2020

(65) Prior Publication Data
US 2022/0073857 A1 Mar. 10, 2022

(30) Foreign Application Priority Data
Dec. 19, 2018 (IT) ........................ 102018000020242

(51) Int. Cl.
*C12M 1/00* (2006.01)
*C12M 1/34* (2006.01)
(Continued)

(52) U.S. Cl.
CPC ............ *C12M 29/04* (2013.01); *C12M 41/36* (2013.01); *C12N 1/20* (2013.01); *C12M 1/125* (2013.01); *C12M 25/04* (2013.01)

(58) Field of Classification Search
None
See application file for complete search history.

(56) References Cited

U.S. PATENT DOCUMENTS

2004/0063206 A1 4/2004 Rowley et al.
2004/0147016 A1 7/2004 Rowley et al.
(Continued)

FOREIGN PATENT DOCUMENTS

WO 2010022151 A1 2/2010
WO 2010118857 A2 10/2010
WO 2016026877 A1 2/2016

OTHER PUBLICATIONS

Lourenço ("Bioengineering a novel 3D in vitro model of gastric mucosa for stomach permeability studies"). Available online Oct. 9, 2018. (Year: 2018).*
(Continued)

*Primary Examiner* — Michael A Marcheschi
*Assistant Examiner* — Nathan G Esperon
(74) *Attorney, Agent, or Firm* — LUCAS & MERCANTI, LLP

(57) ABSTRACT

A three-dimensional substrate with structural and compositional gradient for microbial cultures and cocultures is
(Continued)

provided. The three-dimensional substrate includes a diffusion system having a first apical compartment placed above a second basolateral compartment, the first and second compartments being separated by a semipermeable membrane, a base solution comprising polysaccharides, proteins and salts or a preformed hydrogel comprising polysaccharides, proteins and salts, and a cross-linking medium comprising salts, culture media and distilled water. A method for preparing a three-dimensional substrate with structural and compositional gradient for microbial cultures and cocultures is also provided.

2 Claims, 8 Drawing Sheets

(51) Int. Cl.
*C12N 1/20* (2026.01)
*C12M 1/12* (2006.01)

(56) References Cited

U.S. PATENT DOCUMENTS

| | | | | |
|---|---|---|---|---|
| 2007/0292837 | A1* | 12/2007 | Deutsch | B29C 65/002 435/174 |
| 2010/0047907 | A1* | 2/2010 | Li | C12M 25/04 435/371 |
| 2012/0058551 | A1* | 3/2012 | Marzorati | C12N 11/02 435/297.1 |
| 2017/0189454 | A1* | 7/2017 | Heywood | A61P 37/08 |
| 2017/0328888 | A1* | 11/2017 | Van Vliet | C12M 41/38 |
| 2019/0211296 | A1* | 7/2019 | Allbritton | C12M 25/14 |

OTHER PUBLICATIONS

MacWilliams (“Luria Broth (LB) and Luria Agar (LA) Media and Their Uses Protocol”) (Year: 2016).*

Ma, et al. (“Flow behavior, thixotropy and dynamical viscoelasticity of sodium alginate aqueous solutions”) (Year: 2014).*

International Search Report, issued in PCT/IB2019/061120, mailed Mar. 4, 2020, Rijswijk, Netherlands.

* cited by examiner

A

B

A

B

THREE-DIMENSIONAL SUBSTRATE FOR MICROBIAL CULTURES

CROSS-REFERENCE TO RELATED APPLICATIONS

This application is a U.S. National Phase filing of PCT International Patent Application No. PCT/IB2019/061120, having an international filing date of Dec. 19, 2019, which claims priority to Italian Patent Application No. 102018000020242, filed Dec. 19, 2018 each of which is hereby incorporated by reference in its entirety.

FIELD OF THE INVENTION

The present invention relates to a three-dimensional gradient substrate for microbial cultures and cocultures, and to a method for simultaneously preparing the substrate and the gradient in the same substrate.

In an embodiment, the present invention relates to a three-dimensional substrate for microbial cultures and cocultures, and to a method for preparing it, where said three-dimensional substrate comprises:

- a diffusion system (1) which comprises a first compartment (2) and a second compartment (3), where said first compartment (2) is placed above said second compartment (3), said first and second compartments (2, 3) being separated by a semipermeable membrane (4);
- a base solution which comprises polysaccharides, proteins and salts or a preformed hydrogel which comprises polysaccharides, proteins and salts;
- a cross-linking medium which comprises salts, culture media and distilled water.

BACKGROUND ART

Nowadays, bacterial cultures are typically obtained in agar, with the limitations which come therewith. Among these, it is worth noting that soft agar gels allow some bacterial mobility in addition to the diffusion of substances therein. However, said gels are necessarily positioned on a hard agar base (1.5-2.0% w/v) leading to a three-dimensional migration which is only partial, since limited by said base.

Moreover, pouring soft agar gels into high strength supports such as cell culture plates or multiwell plates for high-throughput screening and result interpretation requires some manipulation and complex structures, thus limiting the screening ability and increasing the risk of contamination.

The need is strongly felt for alternative methods for microbial cultures and cocultures, which are able to mimic both the conditions found in the mucus as well as physiopathological culture conditions.

SUMMARY OF THE INVENTION

It forms a first object of the invention a three-dimensional substrate adapted to study bacterial and/or microbial cultures and cocultures.

In a second object, the present invention describes a method for simultaneously producing the three-dimensional substrate and a gradient therein.

DETAILED DESCRIPTION OF THE INVENTION

In a first object, the present patent application describes a three-dimensional substrate.

In the following description, reference will be made to such a substrate with the term "SUBSTRATE".

The three-dimensional substrate according to the present invention comprises a mixture of components which are able to form a gel using various cross-linking agents by means of a diffusion process. The diffusion process controls the process of forming the gradient.

The authors of the present invention have surprisingly demonstrated that the rheological properties of the SUBSTRATE can be accurately modified by varying the cross-linking parameters.

The "SUBSTRATE" comprises a diffusion system which is a two-compartment system producing a cross-linking gradient (intended as the distance between two cross-linking points) such as to simulate and reproduce the typical diffusion of nutrients and molecules of the microbial microenvironment.

Figure 1:
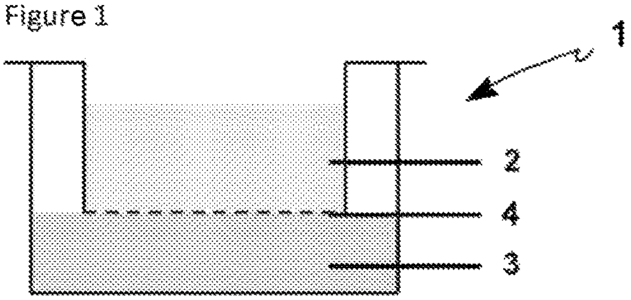
FIG. 1: diagrammatic representation of the diffusion system which contains the three-dimensional substrate of the invention.

With reference to FIG. 1, said diffusion system 1 comprises a first compartment 2 (also called apical) and a second compartment 3 (also called basolateral). In a preferred embodiment of the invention, said first compartment 2 is placed above said second compartment 3. Said first and second compartments are separated from each other by a semipermeable membrane 4. For the purposes of the present invention, said semipermeable membrane 4 is permeable to salts but not to polysaccharides and proteins; for example, such a membrane is not permeable to an alginate and/or mucin solution. In a preferred aspect, said semipermeable membrane 4 is made of a material represented for example by: polycarbonate, polystyrol, poly(diallyldimethylammonium chloride), polyethylene terephthalate or polyamide (nylon).

In a preferred embodiment, said diffusion system 1 is designed by means of a designing software and is produced by three-dimensional printing; alternatively, it is produced by rapid prototyping, processing with additive and subtractive methods, and injection molding. A solution, defined as base solution, is deposited in said first apical compartment 2. For the purposes of the present invention, said base solution comprises polysaccharides, proteins and salts. In an embodiment, said base solution has a viscosity between 0.05 and 100 Pa·s, preferably between 0.2 and 10 Pa·s.

In an alternative embodiment, a preformed gel comprising polysaccharides, proteins and salts can be introduced into the first apical compartment 2 instead of a solution.

In a preferred aspect, the polysaccharides of the base solution are selected from sodium alginate at different molecular weights, pectin at different molecular weights and at different esterification and amidation degrees, hyaluronic acid at different molecular weights, gellan at different molecular weights, dextran at different molecular weights.

In a particularly preferred aspect, the base solution comprises alginate as a polysaccharide.

Alginate is present in an amount of about 0.2-8% and preferably of about 5% (w/v).

In a preferred aspect, the proteins of the base solution are selected from mucin, serum albumin, fibrinogen, fibronectin, collagen, elastin, insulin, transferrin.

In a particularly preferred aspect, the base solution comprises mucin.

Even more preferably, mucin is at a concentration of about 25 mg/mL.

In an even more preferred aspect, in the base solution, mucin and alginate are included in a ratio (weight/weight) of:

| mucin:alginate |
|---|
| 25:2 |
| 25:3 |
| 5:1 |

In a preferred aspect, the salts of the base solution are selected from sodium chloride, ammonium phosphate, potassium chloride, dibasic sodium phosphate, sodium bicarbonate, potassium chloride, dibasic potassium phosphate trihydrate, magnesium chloride hexahydrate, sodium sulfate, tris (hydroxymethyl)aminomethane, sodium nitrate, sodium nitrite, potassium nitrate, silver nitrate, ammonium nitrate, calcium nitrite, potassium bisulfate, potassium sulfate, sodium bisulfate, sodium sulfate and/or copper (I) sulfate.

In a preferred aspect, the salt of the base solution is represented by NaCl, which, in an even more preferred aspect, is present in an amount of about 0.007-9 mg/mL and preferably of about 7 mg/mL.

With regard to the second basolateral compartment 3, a cross-linking medium is deposited therein. For the purposes of the present invention, such a cross-linking medium comprises salts, culture media and distilled water.

In an embodiment, the salts included in the cross-linking medium are selected from calcium acetate, calcium citrate, calcium chloride, calcium glubionate, calcium gluceptate, calcium gluconate, calcium nitrate, calcium phosphate, calcium hydrogen phosphate, hydroxyapatite, carbonate-hydroxyapatite, tricalcium phosphate, octacalcium phosphate, potassium nitrate, zinc nitrate, magnesium nitrate, barium nitrate, titanium nitrate, iron (III) nitrate, copper nitrate, gallium nitrate, calcium nitrite, aluminum sulfate, aluminum sulfoacetate, zinc sulfate, tetraamine copper (II) sulfate, copper sulfate, iron (III) sulfate hydrate, iron sulfate, calcium sulfate and/or magnesium sulfate.

In a preferred aspect, the salt is represented by calcium gluconate which, in an even more preferred aspect, is present in an amount of about 0.05-1.2% (w/v) and preferably of about 0.16% (w/v).

In a preferred aspect, the culture medium is represented by the Muller Hinton and Luria Bertani culture medium.

In an embodiment, the components of the "SUBSTRATE" are dissolved in a bacterial medium which is suitable for the purpose or in a water solution.

Those skilled in the art know how to adapt the thickness of the "SUBSTRATE" by varying the solution volume introduced and the diameter of said first compartment 2.

As reported above, in another embodiment, a preformed hydrogel containing the same components described for the solution is introduced into said first apical compartment (2).

In a second object, in fact, it is described a method of preparing the "SUBSTRATE" of the invention.

In particular, such a method comprises the steps of:

providing a diffusion system (1) which comprises a first compartment (2) and a second compartment (3), where said first compartment (2) is placed above said second compartment (3), said first and second compartments (2, 3) being separated by a semipermeable membrane (4) which is permeable to salts but is not permeable to polysaccharides and proteins;

loading a base solution or preformed hydrogel which comprises polysaccharides, proteins and salts into said first compartment (2);

loading a cross-linking medium which comprises salts, culture media and distilled water into said second compartment (3).

incubating.

In particular, the base solution and the cross-linking medium are those described above.

In particular, the incubation is continued for a sufficient time to allow the diffusion of the salt from the second basolateral compartment (3) through the semipermeable membrane (4) to the first apical compartment and allow the cross-linking. The time also controls the simultaneous formation of the gradient.

For example, the incubation can be continued for a period of time from 2 minutes to 20 hours at a temperature of 4-25° C.

In a preferred aspect, the incubation is continued for 20 hours at a temperature of 4° C.

In a preferred aspect, the "SUBSTRATE" is prepared using a 5% (w/v) alginate solution prepared in a solution of sodium chloride 7.07 mg/ml and 0.16% (w/v) calcium gluconate prepared in the Müller Hinton culture medium to act as a cross-linking agent. Once the solutions were prepared, 500 μL of alginate solution was distributed on the upper chamber of the diffusion device, while 6 ml of 0.16% (w/v) calcium gluconate is introduced into the lower chamber. Finally, the two-compartment diffusion chamber is left at the temperature of about 4° C. for a period of time of 20 hours.

Advantageously, the preparation process does not expose the "SUBSTRATE" to high temperatures or reagents which are incompatible with the loading of eukaryotic or prokaryotic cells, proteins or thermolabile substances.

Again advantageously, the three-dimensional SUBSTRATE obtained for the growth of microorganisms in pure culture or coculture is characterized by a modular cross-linking, gas concentration and composition gradient.

The authors of the present invention have surprisingly demonstrated that, with the addition of human serum albumin to the "SUBSTRATE", the viscoelastic properties thereof increase. This observation is indicative of the fact that not only the protein is not denatured by the "SUBSTRATE", but also that the "SUBSTRATE" allows to reproduce the physiological interactions of albumin in the mucus.

This observation makes the "SUBSTRATE" particularly adavantageous for simulating or reproducing the mucus. In fact, the currently available mucins cannot be cross-linked since, during the extraction and purification process, they lose the cross-linking sites. The gelation of mucins is only possible under conditions of strong acidity, which are incompatible with the microbial cultures. The "SUBSTRATE" allows to produce a hydrogel from commercially available mucins, defined as "Mucin-SUBSTRATE".

The "Mucin-SUBSTRATE" thus obtained was used for evaluating the diffusion of active ingredients through the mucous barrier. It has been shown that the "SUBSTRATE" acts as a barrier towards the diffusion of active ingredients, both in the presence and in the absence of mucin. The "SUBSTRATE" also acts as a barrier towards the diffusion of nanoparticles.

The technology for producing the "SUBSTRATE" permits the application of the process previously described to a preformed hydrogel, thus producing gradients which allow the viscoelastic properties of interest for the specific application to be achieved.

Using the "SUBSTRATE" in antibiograms permits to obtain more reliable results than those achieved by the methods currently used, for computing the Minimum Inhibitory Concentration (MIC) of both single strains and complex cultures (microbial cultures comprising different genera, species or strains). Indeed, the "SUBSTRATE" produces a material which is capable of providing the bacteria with a context adapted to allow them to form aggregates or biofilms, or mimic three-dimensional matrices such as the mucus for recreate phenomena related to the spatial heterogeneity of media. This is possible due to the three-dimensional architecture of the "SUBSTRATE", in addition to the gradient of nutrients, oxygen and water, which factors are not typically modulable in the culture media found in the background art.

In an embodiment, the "SUBSTRATE is separated from the diffusion system where it has been created, and is placed inside supports, e.g. high strength supports, such as cell culture plates or multiwell plates for high-throughput screening, thus allowing to obtain significant data in a short-term analysis and a minor manipulation, thus avoiding cross-contamination.

In an embodiment, the "SUBSTRATE" can be divided into multiwell plates of the desired size.

The following examples are to be considered illustrative of the invention and do not limit it, the scope thereof being defined by the appended claims.

EXAMPLES

Example 1: "SUBSTRATE" Loading with Human Serum Albumin

Figure 2:
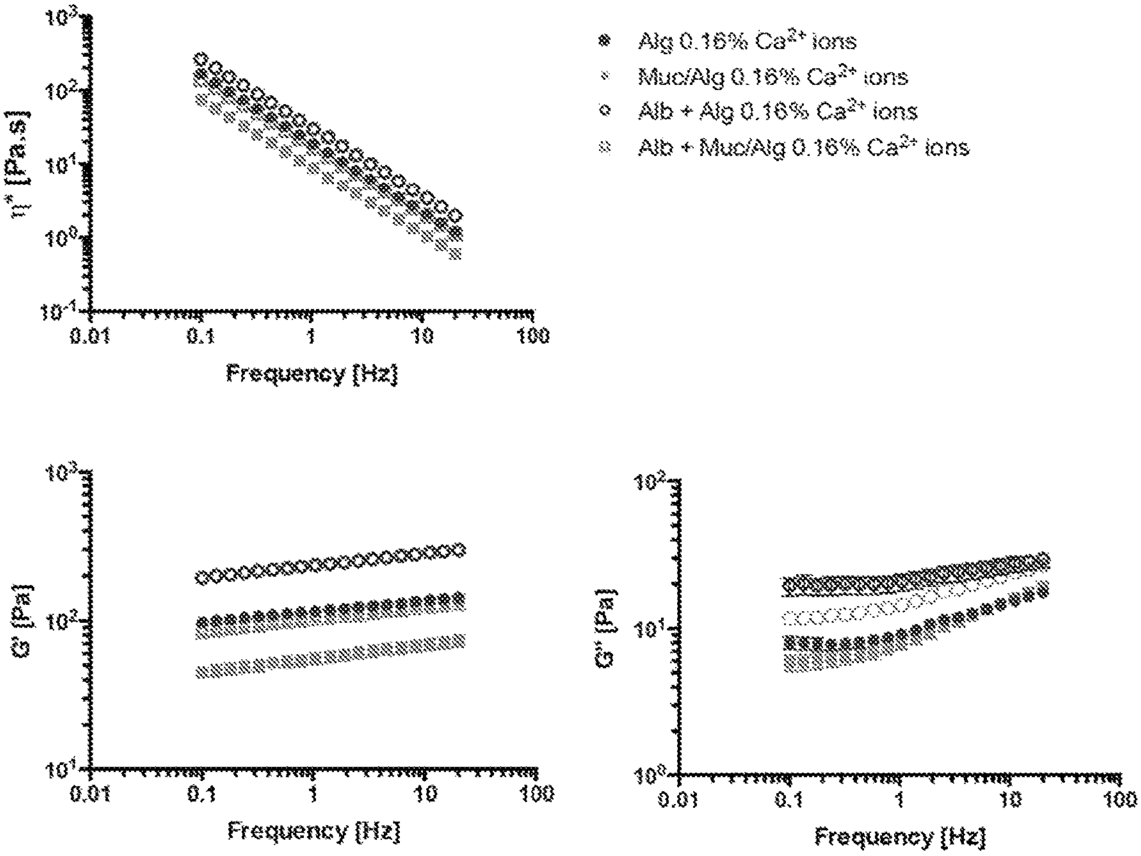
FIG. 2: rheological properties of the three-dimensional gradient substrate of the invention with the addition of human serum albumin.

Human serum albumin (HSA) was added to the alginate solution and to the mucin alginate solution prior to cross-linking, the double syringe method. In short, 10 μL of 56.2 mg/mL HSA solution was mixed with alginate or mucin/alginate solutions to obtain a final concentration of HSA of 1.182 mg/mL. The viscoelastic properties of the hydrogel thus obtained are shown in FIG. 2.

Example 2: Obtaining and Characterizing the "Mucin-SUBSTRATE"

Mucin was added to the "SUBSTRATE" in the amounts shown in Table 1, where mucin concentrations are indicated with reference to the finished product:

TABLE 1

| mucin concentration (mg/mL) | mucin:alginate |
|---|---|
| 25 | 25:2 |
| 25 | 25:3 |
| 25 | 5:1 |

Commercially available porcine gastric mucin was dissolved in an aqueous solution of NaCl (16.33 mg/mL) at a concentration of 25 mg/mL. After stirring overnight at 4° C., alginate powder was added until the desired concentration indicated in Table 1 was achieved and stirred until completely dissolved.

The hydrogel was formed using the two-compartment diffusion system. Briefly, 200 μL of mucin/alginate solution was introduced into the apical chamber of the diffusion system (diameter=1.5 cm, thickness≈120 μm) and left at 4° C. for 20 hours in order to allow the diffusion of $Ca^{2+}$ ions from the calcium gluconate solution loaded in the lower chamber. The thickness of the "SUBSTRATE" is adapted as required by varying the solution volume introduced and the diameter of said first compartment 2.

Figure 3:
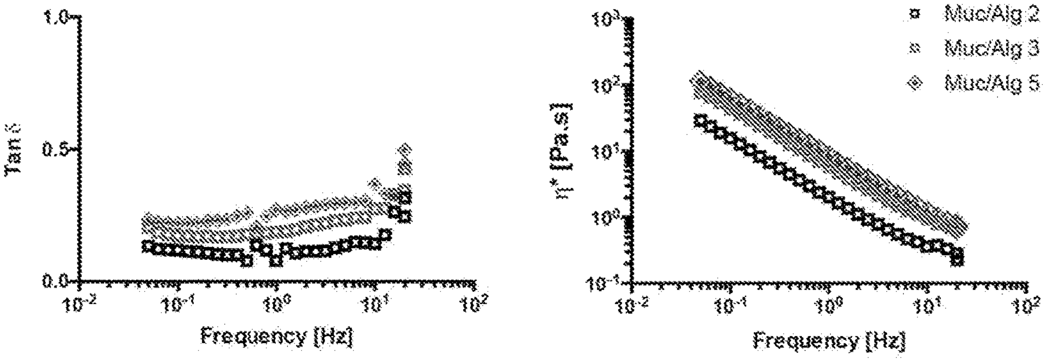
FIG. 3: shows the possibility of varying the viscoelastic properties of the three-dimensional substrate according to an embodiment of the invention (Mucin-SUBSTRATE).

The viscoelastic properties are then measured, and the data obtained are shown in FIG. 3.

The data obtained show the possibility offered by the system according to the present invention of optimizing the viscoelastic properties of mucin-based hydrogels by controlling the cross-linking degree, such as the cross-linking time and the cross-linker concentration, and the concentration of polysaccharide and the molecular weight thereof. An example of property variation upon varying the alginate concentration is shown in FIG. 3.

Example 3: "SUBSTRATE" and "Mucin-SUBSTRATE2" ($Mus^3SUB$) Such as Mucous Barrier Model "SUBSTRATE" and Mus SUB with the features referred to in Example 2 were tested for the ability thereof to mimic the mucous barrier.

The active ingredients Cefalexin and Epirubicin, in addition to gold nanoparticles, were tested.

The gold nanoparticles have a steric hindrance of about 25 nm, Cefalexin of about 3 nm, and Epirubicin of about 4 nm.

Figure 4:
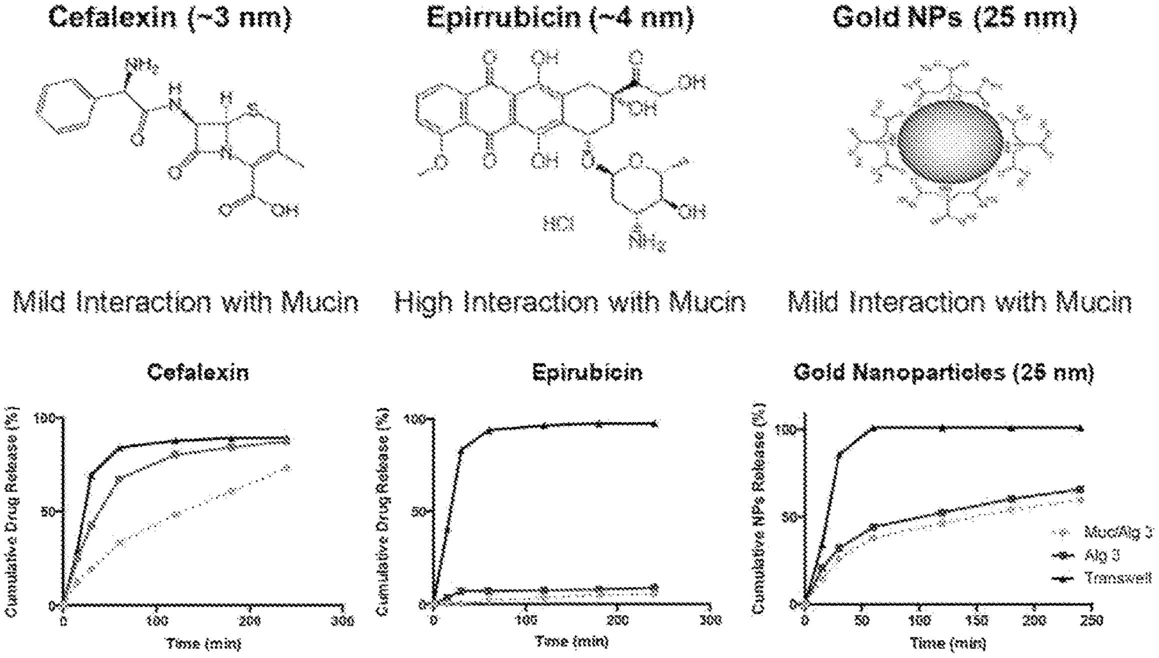
FIG. 4: barrier effect against the diffusion of active ingredients and nanoparticles.

The charts in FIG. 4 show the ability of said molecules to cross a barrier, where the barrier consists of a permeable support, "SUBSTRATE" or $Mus^3SUB$.

The results show that if the drug has a strong interaction with mucin, such us in the case of Epirubicin (pka=8.01, logD7.4=0.03), the transition of the drug is slowed. Instead, in case of low interaction with mucin, such as in the case of Cefalexin (pka=3.26 and 7.23, logD7.4=−2.5), the transition is very quick. This shows the ability to act as an interactive barrier, thus allowing the mucin in the "SUBSTRATE" to retain the ability thereof to interact with the molecules.

The interaction being equal, the steric barrier effect can be pointed out: from the comparison between gold nanoparticles (25 nm) and Cefalexin (3 nm), it is noted that larger gold nanoparticles are slowed down by the presence of the "SUBSTRATE".

Example 4: Obtaining the "SUBSTRATE" with Viscoelastic Properties and Differential Gradients A "SUBSTRATE" produced from a previously cross-linked hydrogel is indicated with "double".

Figure 5:
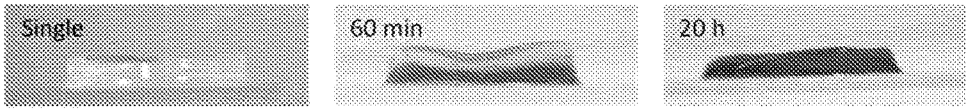
FIG. 5: A) the three-dimensional substrate of the invention stained with alizarin red to represent the internal cross-linking gradient thereof; B) variation of the viscoelastic properties controlled by the various cross-linking times.
Figure 5:
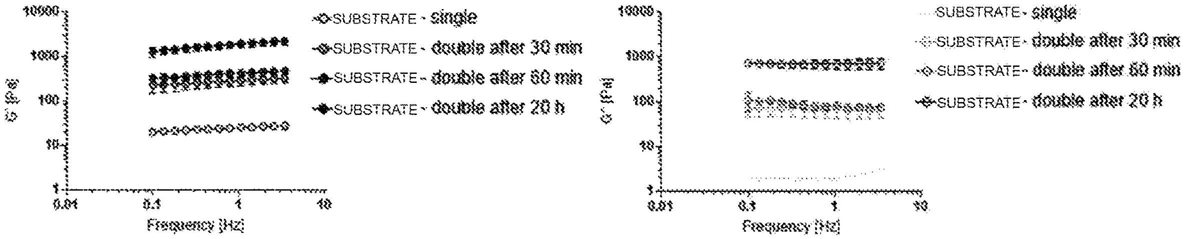

Some "SUBSTRATES" were produced inside the two-compartment diffusion system with different cross-linking times, in order to produce a double cross-linking structure. In short, sodium alginate was dissolved at 2.8% (w/v) in NaCl solution (16.33 mg/ml), under slow magnetic stirring for 12 hours. The alginate solutions and distilled water were mixed in a 1:4 ratio by using the double syringe method (step 1). A suspension of calcium carbonate 7 mg/mL) in NaCl solution (16.33 mg/mL) was subjected to ultrasounds (UP200S, ultrasonic processor, Hielscher, Ultrasound Technology) for 5 minutes, centrifuged (Vortex IKA MS3 100-240 V orbital stirrer) at 3500 rpm for 1 min, and further mixed with the solution prepared in step 1 in a 1:5 ratio (step 2). Finally, a GDL solution (10 mg/mL) was prepared in NaCl (16.33 mg/mL) and mixed with the solution prepared in step 2 in a 1:6 ratio. Approximately 706 μL of the final mixture was inserted into the first apical compartment and this mixture was allowed to react overnight ("SUBSTRATE"-single). After cross-linking overnight, 0.2% calcium gluconate or calcium chloride was dissolved in 40 mM of alizarin red and 6 mL of this solution was introduced into the second basolateral compartment and allowed to react for a different time, for example for 5, 30 and 60 minutes, as well as for 20 hours in order to allow the production of a gradient ("SUBSTRATE"-double). Alizarin red is an organic red stain used for identifying calcium deposits in the cell culture with a well-defined staining protocol. As seen in FIG. 5A, the diffusion of calcium gluconate leads to the formation of a calcium gradient inside the "SUBSTRATE", with deep red or mixed areas (at the bottom and top of the samples, respectively), while "SUBSTRATE"-single was clear and "SUBSTRATE"-double after 20 hours of second cross-linking showed a homogeneous red color (black in the figure).

The viscoelastic changes induced by the second cross-linking of the "SUBSTRATE" were also analyzed (FIG. 5B). Both conservative and dissipative modules increased with the time of the second cross-linking, which was more noticeable between 60 minutes and 20 hours. In fact, the maximum values of the conservative module were detected for the sample exposed to 20 hours of diffusion and no significant differences were found between 30 and 60 minutes of diffusion.

Example 5: "SUBSTRATE" Simulates a Physiological or Pathological Context

A bacterial starter culture was inoculated into the appropriate medium and cultured overnight. In order to inoculate the starter culture, in this case *Pseudomonas aeruginosa*, a small amount of frozen bacterial material was mechanically removed from the original cryovial, stored at −80° C., and suspended in 10 mL of Mueller Hinton (MH) medium, then kept at 37° C. under stirring at 200 rpm overnight.

On the next day, the estimation of the number of bacteria was spectrophotometrically performed at λ=600 nm (Optical Density600; OD600). In order to prepare the samples for the absorbance test, the suspension was eluted in a 1:10 ratio with fresh MH medium. The same medium was used as a blank. Once the absorbance of the diluted sample was measured, the number of bacteria was estimated using a calibration curve showing the number of bacteria with an OD600 value. This concentration was then corrected for the undiluted volume.

In order to test the bacterial viability inside the "SUBSTRATE", each "SUBSTRATE" was infected with 500, 1000 and 5000 bacteria for 24 and 48 hours of incubation. To that end, 1 mL of suspension was taken from the initial starter culture and diluted at the concentrations required. The "SUBSTRATE" was then infected by introducing 100 μL of bacterial suspension and allowed to incubate under static conditions at 37° C. CFU counts were used to study the presence of bacteria within the "SUBSTRATE", i.e. the bacteria which had migrated and effectively proliferated inside the "SUBSTRATE" as a comparison with the bacteria cultured under planktonic conditions. In this case, the axenic cultures were conducted both under planktonic conditions and in the "SUBSTRATE".

In order to estimate the number of bacteria migrated and proliferated inside the "SUBSTRATE", the residual bacteria found on the top of the "SUBSTRATE" and on the walls of the well were removed by means of two washings with fresh MH medium. The "SUBSTRATE" was then dissolved using a 50 mM sodium citrate solution at pH 7.4. After dissolution, the suspension was eluted and plated after the CFU count. In short, the medium was introduced into a 1.5 mL centrifuge tube and then diluted in [$10^{-6}$-$10^{-10}$]-fold dilutions in 0.9% aqueous solution of aqueous sodium chloride solution, pH 7.4. 10 μl of the diluted suspension was then uniformly distributed on MH Agar plates.

Figure 6:
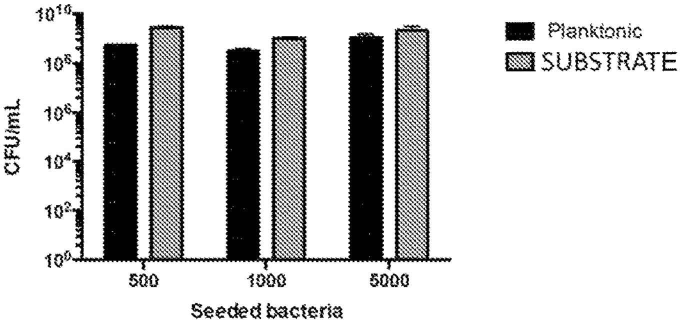
FIGS. 6: A) and B) show the possibility of culturing *Pseudomonas aeruginosa* CFU/mL evaluated on the three-dimensional substrate of the invention with viability comparable to planktonic cultures.
Figure 6:
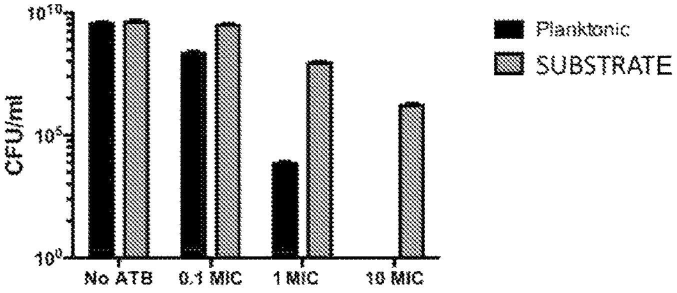

The MH agar plates were left in the incubator overnight. The actual colonies inside the infected "SUBSTRATE" were calculated by multiplying by the dilution factor. In the case of the "SUBSTRATE", 150 μL of dissolving agent was considered in order to calculate CFU/mL. The results are shown in FIG. 6A.

In a further experiment, the "SUBSTRATE" was seeded with $10^4$ bacteria/mL, required to obtain $10^8$ bacteria after 24 hours. After this period, the supernatant on the "SUBSTRATE" was removed and the "SUBSTRATE" was washed twice with fresh culture medium. 100 μL of antibiotic at three concentrations, that is 0.1 MIC, 1 MIC and 10 MIC, was then added. The antibiotic was allowed to act for 24 hours under static incubation at 37° C.

After an effective antibiotic action time, a viable CFU count was performed. Various controls were carried out: (I) planktonic bacteria at each concentration of antibiotics; (II) planktonic bacteria without any treatment; (III) untreated infected "SUBSTRATE"; and (IV) solutions for the formation of "SUBSTRATE". With regard to the infected "SUBSTRATE" tested with antibiotics, even in the latter case, only the CFUs of dissolved "SUBSTRATE" were taken into account. The data obtained are shown in FIG. 6B.

Example 6: *Escherichia coli* is Added to the "SUBSTRATE" Prepared as Described in Example 5 ("SUBSTRATE"-Single)

A bacterial starter culture was previously inoculated into Luria-Bertani (LB) broth and cultured overnight. In order to inoculate the starter culture, in this case *Escherichia coli*, a small amount of frozen bacterial material was mechanically removed from the original cryovial, stored at −80° C., and suspended in 10 mL of Luria-Bertani (LB) broth medium, then kept at 37° C. under stirring at 200 rpm overnight.

On the next day, the estimation of the number of bacteria was spectrophotometrically performed at λ=600 nm (Optical Density600; OD600). In order to prepare the samples for the absorbance test, the suspension was eluted in a 1:10 ratio with fresh medium. The same medium was used as a blank. Once the absorbance of the diluted sample was measured, the number of bacteria was estimated using a calibration curve showing the number of bacteria with an OD600 value. This concentration was then corrected for the undiluted volume.

In order to test the bacterial viability inside the "SUBSTRATE", each "SUBSTRATE" was infected with 500, 1000 and 5000 bacteria for 24 hours of incubation. To that end, 1 mL of suspension was taken from the initial starter culture and diluted at the concentrations required. The "SUBSTRATE" was then infected by introducing 100 μL of bacterial suspension and allowed to incubate under static conditions at 37° C.

CFU counts were used to study the presence of bacteria within the "SUBSTRATE", i.e. the bacteria which had migrated and effectively proliferated inside the "SUBSTRATE" as a comparison with the bacteria cultured under planktonic conditions. In this case, the axenic cultures were conducted both under planktonic conditions and in the "SUBSTRATE".

In order to estimate the number of bacteria migrated and proliferated inside the "SUBSTRATE", the residual bacteria found on the top of the "SUBSTRATE" and on the walls of the well were removed by means of two washings with fresh medium. The "SUBSTRATE" was then dissolved using a 50 mM sodium citrate solution at pH 7.4. After dissolution, the suspension was eluted and plated after the CFU count. In short, the medium was introduced into a 1.5 mL centrifuge tube and then diluted in [$10^{-6}$-$10^{-10}$]-fold dilutions in 0.9% aqueous solution of aqueous sodium chloride solution, pH 7.4. 10 μl of the diluted suspension was then uniformly distributed on LB Agar plates.

Figure 7:
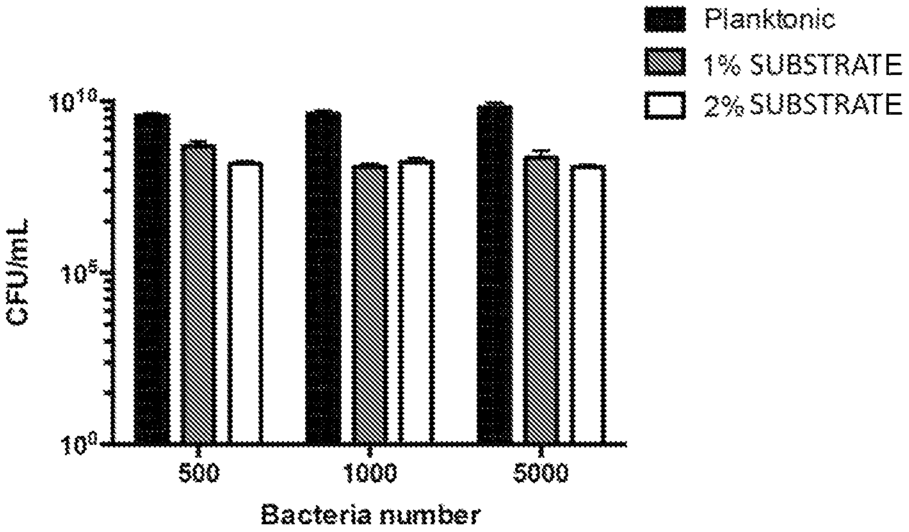
FIG. 7: shows the possibility of culturing *Escherichia coli* CFU/mL evaluated on the three-dimensional substrate of the invention with viability comparable to planktonic cultures.

The LB agar plates were left in the incubator overnight. The actual colonies inside the infected "SUBSTRATE" were calculated by multiplying by the dilution factor. In the case of the "SUBSTRATE", 150 μL of dissolving agent was considered in order to calculate CFU/mL. The results are shown in FIG. 7.

Various controls were carried out: (I) planktonic bacteria at each concentration of antibiotics; (II) "SUBSTRATE" without infection; and (III) solutions for the formation of "SUBSTRATE".

Example 7

The "SUBSTRATE" of the invention was produced using a 5% (w/v) alginate solution prepared in a solution of sodium chloride (7.07 mg/ml) and 0.16% (w/v) calcium gluconate prepared in the Müller Hinton culture medium as a cross-linking agent. Once the solutions were prepared, 500 L of alginate solution was placed in the upper chamber of the diffusion device, while 6 mL of 0.16% (w/v) calcium gluconate was introduced into lower chamber. Finally, the two-compartment diffusion chamber was stored at 4° C. overnight for 20 hours.

Figure 8:
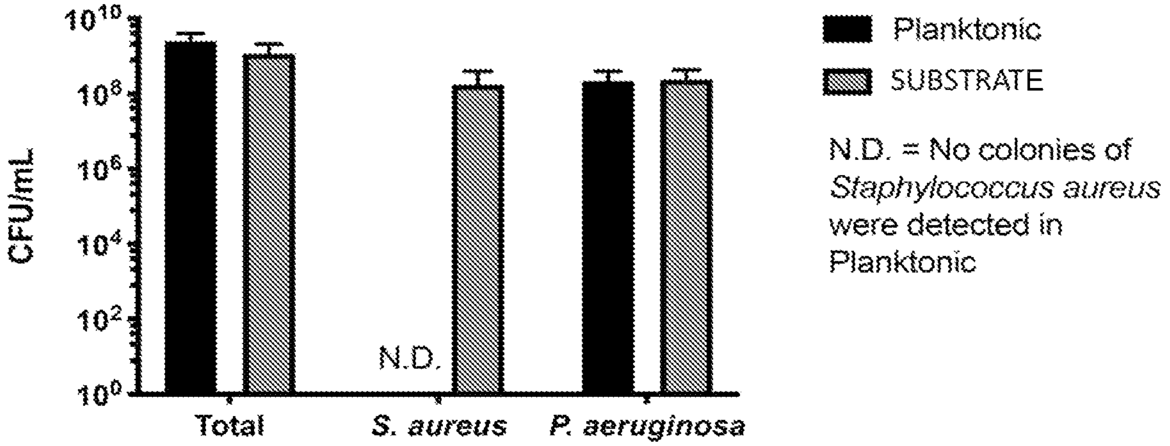
FIG. 8: shows the ability to reproduce the simultaneous presence of several bacterial strains, similarly to the case of chronic co-infections (results of Example 7) and differently from case of suspensions in a liquid (planktonic) medium.

In parallel, a bacterial culture was inoculated and cultured overnight. In order to inoculate the culture, a small amount of frozen bacterial material was mechanically removed from the original cryovial (stored at −80° C.) suspended in 10 mL of Müller Hinton culture medium and kept at 37° C. and 200 rpm. After the night inoculation, the number of bacteria was spectrophotometrically quantified at λ=600 nm (OD600). Both *Staphylococcus aureus* ATCC 25923 and *Pseudomonas aeruginosa* PAO1 ATCC 15692 were cultured on the substrate and under planktonic conditions in a 1:1 ratio and incubated at 37° C. for evaluating the bacterial growth inside the substrate. In short, the "SUBSTRATE" was infected with 100 μL 103 *S. aureus* and *P. aeruginosa* in a 1:1 ratio. After 24 hour of culture, 150 μL of 50 mM tribasic sodium citrate dehydrate, pH 7.4, was used for dissolving the substrate. After 2 minutes of reaction, the new suspension was eluted in [10−6, 10−10]-fold dilutions in 0.9% NaCl solution, pH 7.4. 10 μL of the diluted suspension was then uniformly distributed on Müller Hinton medium agar plates, which were incubated overnight at 37° C. The colony forming units (CFUs) were then calculated while taking into account the dilution factor. The results are shown in FIG. 8.

In suspension in the culture medium (planktonic conditions), S. *Aureus* cannot be cultured in the co-presence of P. *Aeruginosa*. Only P. *Aeruginosa* is counted (black bars) while *S. aureus* is not detectable (ND in FIG. 8). If the cocultures are conducted on the substrate of the invention (gray bar), both bacteria are viable and capable of forming colonies. This result indicates the possibility of representing conditions of simultaneous presence of infection of the two bacteria in chronic infections and studying the competitive effects only in case of use of the substrate of the invention, and not under standard culture conditions.

Example 8

The "SUBSTRATE" of the invention was produced using a 5% (w/v) alginate solution prepared in a solution of sodium chloride 7.07 mg/ml and 0.16% (w/v) calcium gluconate prepared in the Müller Hinton culture medium to act as a cross-linking agent. Once the solutions were prepared, 250 or 500 μL of alginate solution was distributed on the upper chamber of the diffusion device, while 6 mL of 0.16% (w/v) calcium gluconate was introduced into the lower chamber. The "SUBSTRATE" produced using 250 μL of alginate solution was designated as "thin", while those produced using 500 μL are called "thick. Finally, the two-compartment diffusion chamber was stored at 4° C. overnight for 20 hours.

The $O_2$ tension inside the "SUBSTRATE" was measured using a Clark-type oxygen sensor (OX-25; Unisense, Aarhus N, Denmark), connected to a high sensitivity picoampere four-channel amplifier referred to as a Microsensor Multimeter S/N 8678 (Unisense). $O_2$ diffuses from the environment through a silicone membrane with sensor tip and is reduced on the surface of the golden cathode thus producing electric current. The picoammeter converts the resulting reduction current into a signal. The signal from the oxygen sensor is generated in picoamperes. Therefore, the oxygen sensor needs to be connected to a picoampere amplifier during the measurements. The Unisense SensorTrace software then automatically converts the signal from the partial pressure (oxygen tension) to the equivalent oxygen concentration in μmol/L.

Before starting the measurements, the electrodes, i.e. the reference anode and the protective cathode, were polarized overnight and further calibrated in air-saturated water (positive control), as well as in 2% w/v sodium hydrosulfite (negative control). Prior to the measurements, low melting point agarose consisting of 2% (w/v) agarose in 7.07 mg/mL NaCl was placed in a Petri dish. The freshly prepared "SUBSTRATE" was placed on top of the agarose layer. The microelectrodes were positioned using a motorized micromanipulator (MXU2; PyroScience, Aquisgrana, Germany). The measurements were carried out in the center of the "SUBSTRATE" from their surface (0 mm) through their thickness, until the tip has completely penetrated the entire structure. In order to avoid the oxygen from diffusing through the sides of the "SUBSTRATE", an O-ring was employed, the inner diameter of which corresponded to the diameter of the "SUBSTRATE". The maximum depth reached by the tip, referred to as the final depth, was of about 2200 and 3200 μm for thin and thick "SUBSTRATE", respectively. The consecutive points were taken 100 μm apart. Three replicates were run for each point.

Figure 9:
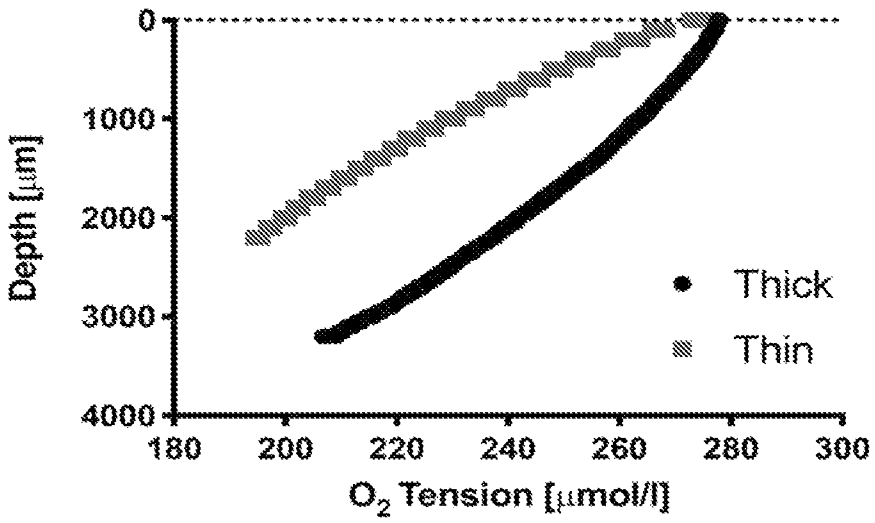
FIG. 9: shows the possibility of controlling the oxygen tension profile of the substrate of the invention.

The results are shown in FIG. 9.

A continuous decrease in oxygen tension was observed throughout the thickness of both types of "SUBSTRATE" with variations of 83.0 and 70.3 μmol/L for thin and thick "SUBSTRATE", respectively. A greater decrease in oxygen tension was found for the thinner "SUBSTRATE". This result indicates the possibility of obtaining oxygen gradients inside the same substrate.

Example 9

The "SUBSTRATE" of the invention was produced using a 5% (w/v) alginate solution prepared in a solution of sodium chloride 7.07 mg/mL and 0.16% (w/v) calcium gluconate prepared in the Müller Hinton culture medium to act as a cross-linking agent. Once the solutions were prepared, 500 μL of alginate solution was distributed on the upper chamber of the diffusion device, while 6 mL of 0.16% (w/v) calcium gluconate was introduced into the lower chamber. Finally, the two-compartment diffusion chamber was stored at 4° C. overnight for 20 hours.

In parallel, a bacterial culture was inoculated and cultured overnight. In order to inoculate the culture, a small amount of frozen bacterial material was mechanically removed from the original cryovial (stored at −80° C.) suspended in 10 mL of Müller Hinton culture medium and kept at 37° C. and 200 rpm. After the night inoculation, the number of bacteria was spectrophotometrically quantified at λ=600 nm (OD600). 100 μL *P. aeruginosa* PAO1 ATCC 15692 was cultured on the "SUBSTRATE" with a number of bacteria equal to 103, and after 12, 24 and 48 hours of infection, the oxygen tension was measured as described in Example 2.

Figure 10:
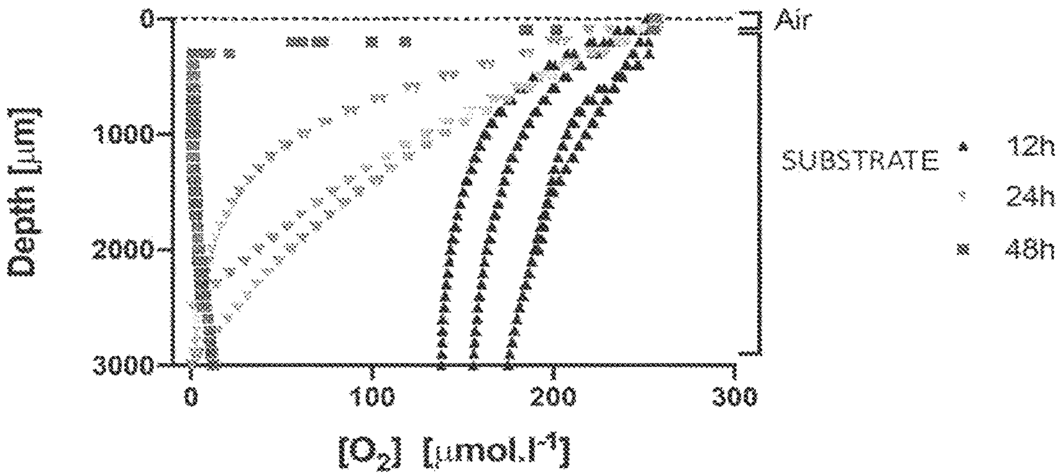
FIG. 10: shows how the bacteria are able to respond to the oxygen gradients found, by modifying the profile (results of Example 9).

The results are shown in FIG. 10.

The oxygen tension profile inside the "SUBSTRATE" continuously decreases with the incubation time, achieving the anoxic conditions after 48 hours at about 300 μm of depth. As the culture time increases, such as from 12 to 24 hours, for example, the oxygen tension difference between the most superficial layers and the innermost layers becomes progressively more marked. This result indicates the synergy of bacteria with the matrix of the "SUBSTRATE" in recreating culture conditions which are more suitable for the specific type of bacteria.

Example 10

The "SUBSTRATE" of the invention was produced using a 5% (w/v) alginate solution prepared in a solution of sodium chloride 7.07 mg/ml and 0.16% (w/v) calcium gluconate prepared in the Müller Hinton culture medium to act as a cross-linking agent. Once the solutions were prepared, 500 μL of alginate solution was distributed on the upper chamber of the diffusion device, while 6 mL of 0.16% (w/v) calcium gluconate was introduced into the lower chamber. Finally, the two-compartment diffusion chamber was stored at 4° C. overnight for 20 hours.

In order to express a fluorescent protein, *P. aeruginosa* PA01 was transformed with a plasmid according to the process suggested by Cadoret et al. (2014).1 Briefly, electroporation of electrocompetent *P. aeruginosa* and fluorescent plasmid pMF440. *P. aeruginosa* was subjected to electroporation by means of a series of dilution steps in the electroporation buffer (sucrose solution 300 mM) from a culture overnight in Luria Bertani (LB). The culture overnight was pelletized and re-suspended in the electroporation buffer. The suspension was then re-centrifuged and re-suspended at half the initial culture volume with fresh electroporation buffer. This process was repeated until the volume was reduced to 0.01 of the initial volume. These steps aimed at providing the bacteria with a nutrient-rich environment for the growth thereof without the presence of ions which could create electric arcs in the electroporation process. Plasmid pMF440 was acquired from the database Addgene (ID code: 62550) as bacterial transformation of *Escherichia coli* DH5α. For the extraction of plasmid DNA, *E. coli* was cultured in LB with 100 μg/mL ampicillin. Plasmid DNA was extracted using the QIAprep Spin Miniprep (Quiagen) kit according to the manufacturer's instructions. After extraction, the DNA was eluted in MilliQ water and stored at −20° C. until needed. The DNA was eluted in deionized water to achieve concentrations between 0.1 and 1 μg/mL. 80 mL of competent *P. aeruginosa* cell suspension was mixed with 10 mL of DNA suspension, and this suspension was kept on ice for 30 minutes prior to electroporation.

The electroporation process was conducted in a gene pulser electroporation system, using a conductive cuvette. The electrical impulse was given for 5 ms at 2.5 kV, 2002, 25 μF. After the shock, the cuvette content was transferred to a Falcon tube containing 2 mL optimal glucose-enriched broth and allowed to incubate under stirring conditions for 2 hours at 37° C. After two hours of recovery, the suspension was plated in selective agar plates containing 300 μg/mL carbenicillin. Further culture and expansion of the transformed bacteria were performed in a medium containing carbenicillin.

A bacterial culture was inoculated and cultured overnight. In order to inoculate the culture, a small amount of frozen bacterial material was mechanically removed from the original cryovial (stored at −80° C.) suspended in 10 mL of Müller Hinton culture medium and kept at 37° C. and 200 rpm. After the night inoculation, the number of bacteria was spectrophotometrically quantified at λ=600 nm (OD600).

100 μL out of 103 of *Pseudomonas aeruginosa* PACC 1 ATCC 15692 expressing green was cultured on the "SUBSTRATE" and incubated at 37° C. The bacterial organization was evaluated by confocal microscopy. After 24 hours of incubation, the samples were observed under a confocal laser microscope. The scanning was performed with excitation having a wavelength of 587 nm and a maximum depth of about 50 μm. The images obtained were analyzed using the LasX software supplied by Leica.

Figure 11:
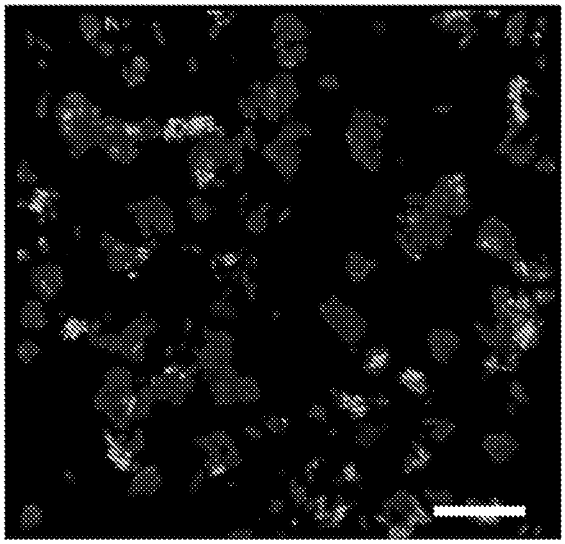
FIG. 11: shows the presence of aggregates similar to those identified in chronic infections (results of Example 10, the bar corresponds to 10 μm).

The results are shown in FIG. 11.

The "SUBSTRATE" allows the formation of bacterial aggregates similar to those observed in human infections, while these aggregates cannot be obtained under suspension culture conditions. The bacteria respond to the gradient by organizing themselves in multicell aggregates which are similar in morphology and size to those previously observed in cystic fibrosis sputum and chronic wounds. These bacterial aggregates are associated with oxygen gradients which then lead to the production of alginate by *P. aeruginosa*, the latter being considered as the cause underlying chronic infections by this pathogen.

From the above description, the advantages of the present invention will become immediately apparent to those skilled in the art.

The "SUBSTRATE" according to the present invention has features such as to become beneficial in applications in the food, environment and health field. The "SUBSTRATE" is also used in the field of the production of products related to bacteria, such as by way of example cellulose, polyesters, insulin, antibacterials, antifungals, antivirals, antithrombotics, immunomodifiers, anticancer agents, enzyme inhibitors, insecticides, herbicides, fungicides (e.g. alkaloids and flavonoids) and substances which promote the growth for plants and animals. By way of example, the "SUBSTRATE" is beneficially used in analyses aimed at monitoring the bacterial growth, the interaction between microbial communities and/or the antimicrobial potential of drugs and micro/nanoparticles, pollutants, probiotics, release of probiotics. Moreover, said three-dimensional substrate is suitable for the screening procedures for selecting effective antimicrobial treatments, as well as for the initial steps in the search for new drugs in addition to the aerospace research to understand the microbial adaptations to the space environment, such as microgravity and high radiation levels. Further applications are in the food industry, for example to understand how certain dietary regimens and/or probiotics affect the bacterial behavior and the microbial communities, as well as a probiotic-carrying agent as a food supplement and in the environmental sciences, for example to evaluate the effect of pollutants or biocidal agents in cleaning products with respect to the microbial communities, as a product for improving agricultural production or for the remediation of environmental contamination. Another example includes the cosmetic field, such as cosmetic products which release microorganisms with dermatological effects. The "SUBSTRATE" may also be utilized as a way for reproducing the microenvironment of microorganisms within microbial pads for treating waters and reducing pollution. The simultaneous culture of different microorganisms inside the three-dimensional substrate can be utilized in the production of biofuels and bioenergetic conversion, since the microorganisms for these applications require a physical and spatial organization. Finally, the three-dimensional substrate can be utilized as a microbiological fuel cell.

The use of the three-dimensional substrate described herein is immediately understandable, and does not require any technical experience or specific equipment. Moreover, the three-dimensional substrate according to the present invention is compatible with commonly used platforms, such as conventional multiwell plates with 6, 12, 24, 48, 96 or 384 wells, Transwell® systems and microfluidic devices. Said three-dimensional substrate has an absolutely competitive cost, and the production thereof is scalable and modular, where the viscoelastic properties and the respective gradient thereof can be easily modified according to the purpose of the study.

The experiments conducted using the three-dimensional substrate according to the present invention have led to realistic results having high reproducibility.

The "SUBSTRATE" has further advantages compared to synthetic or agar-based materials, which advantages are summarized in the following paragraphs:

The components can be carbon sources for the bacteria, and in some cases are produced by the bacteria themselves, for example *Pseudomonas aeruginosa* secrete alginate.

The "SUBSTRATE" allows to culture the bacteria in a three-dimensional gradient structure, which is not shown by the current methods.

The microorganisms cultured in the "SUBSTRATE" can be placed in high strength supports (such as high throughput screening plates), thus allowing to obtain significant data in a short-term analysis and a minor manipulation, thus preventing cross-contamination.

The preparation process avoids using high temperatures or reagents which are incompatible with the encapsulation of microorganisms (e.g. cells of bacteria) or stratified on a cell monolayer.

The preparation process avoids using high temperatures or reagents which are incompatible with the loading of eukaryotic or prokaryotic cells, proteins or thermolabile substances.

Controlling the reaction kinetics of the "SUBSTRATE" allows the latter to be divided effectively in multiwell plates of different size, from plates with 6-96 or 384 wells.

The agar gels which are available from the prior art, in particular 0.2-0.8% w/v agar gels, are a possibility for microbial cultures in three dimensions, but have several limitations:

they show no gradients and are placed on 2D hard agar plates;

soft agar gels show the possible bacterial mobility and the diffusion of the substance into the gel. However, they are positioned on a hard agar base (1.5-2.0% w/v). This allows the cells to migrate partially in three dimensions, since they will be blocked from the level to the base.

Pouring the soft agar gel into high strength supports (high throughput screening plates) and interpreting the results would require manipulation and complex structures, therefore the possibility of contamination would increase and the screening ability in conjunction with the cost-effectiveness would be limited compared to the "SUBSTRATE".

Agar needs to be boiled for a complete dissolution and kept at 50-55° C. to maintain it in liquid form before inoculation and plating. These temperatures are hostile to many microorganisms and will affect the thermolabile components which may be needed to enrich the culture structure (e.g. proteins and vitamins). The "SUBSTRATE" was conceived for synthesis and polymerization under conditions which do not affect the thermolabile components or the encapsulation of microorganisms (e.g. bacteria cells) or stratified on a cell monolayer.

Finally, the three-dimensional substrate according to the present invention, consisting of water-soluble polymers of natural origin and produced without using toxic solvents, is an environment-friendly device.

The invention claimed is:

1. A three-dimensional gradient substrate for microbial culture comprising a gel with a cross-linking gradient obtained by:

contacting a base solution and a cross-linking medium via a semipermeable membrane, wherein the base solution is located above the semipermeable membrane and the cross-linking medium is located below the semipermeable membrane;

incubating the base solution with the cross-linking medium between 2 min and 20 h at a temperature between 4° C. to 25° C. to allow diffusion of salts and a culture medium thereby forming the gel with the cross-linking gradient; and removing the gel, wherein the base solution comprises a polysaccharide selected from the group consisting of:

sodium alginate and pectin, a protein selected from the group consisting of: mucin and serum albumin, and sodium chloride, and the cross-linking medium comprises a salt selected from the group consisting of: calcium chloride and calcium gluconate, the culture medium selected from the group consisting of: Mueller Hinton and Luria Bertani, and distilled water, wherein the culture medium and the salt range from a higher concentration at the bottom side of the three-dimensional gradient substrate to a lower concentration at the surface of the three-dimensional gradient substrate, wherein an oxygen tension is from 150 μmol/L to 210 μmol/L in a deepest region of the gel, and wherein the three-dimensional gradient substrate comprises a storage modulus G' between 45 Pa and 300 Pa for shear strain frequencies from 0.1 Hz to 20 Hz, and wherein the three-dimensional gradient substrate has a thickness greater than 2 mm and equal to or less than 3 mm.

2. The three-dimensional gradient substrate of claim 1, wherein in the base solution, the polysaccharide is sodium alginate and the protein is mucin; and wherein in the cross-linking medium, the salt is calcium gluconate.

* * * * *